(12) United States Patent
Chiang et al.

(10) Patent No.: US 8,187,211 B2
(45) Date of Patent: May 29, 2012

(54) PIVOT MECHANISM FOR A JOINT SUPPORT

(75) Inventors: Pang-Ching Chiang, Taipei (TW); Kuo-Wei Lee, Taipei (TW)

(73) Assignee: Plus Meditech Co., Ltd., Tainan (TW)

( * ) Notice: Subject to any disclaimer, the term of this patent is extended or adjusted under 35 U.S.C. 154(b) by 455 days.

(21) Appl. No.: 12/586,216

(22) Filed: Sep. 18, 2009

(65) Prior Publication Data

US 2011/0071450 A1 Mar. 24, 2011

(30) Foreign Application Priority Data

Jun. 10, 2009 (TW) ................................ 98210298 U (51) Int. Cl.
*A61F 5/00* (2006.01)
*E05D 7/00* (2006.01)
*E05D 7/08* (2006.01)

(52) U.S. Cl. ................................ 602/16; 16/221; 49/388

(58) Field of Classification Search .......... 602/1, 16–18, 602/5, 23, 26, 27, 28; 16/334, 368, 369, 16/221, 321, 319; 49/188, 388, 397
See application file for complete search history.

(56) References Cited

U.S. PATENT DOCUMENTS

| | | | | |
|---|---|---|---|---|
| 4,697,583 | A * | 10/1987 | Mason et al. ................ | 602/26 |
| 5,921,946 | A * | 7/1999 | Tillinghast et al. ............ | 602/16 |
| 7,887,496 | B2 * | 2/2011 | Kahlmeyer et al. ............ | 602/16 |

* cited by examiner

*Primary Examiner* — Patricia Bianco
*Assistant Examiner* — Tarla Patel
(74) *Attorney, Agent, or Firm* — William E. Pelton, Esq.; Cooper & Dunham LLP (57) ABSTRACT

A pivot mechanism for a joint support has a connector, a first support and a second support. The connector has multiple slots. The first support and the second support are mounted pivotally in the connector and rotate synchronously, and each has a protrusion. The protrusions are adjusted to mount in the slots of the connector and to limit an angle between the first and second support to a determined range. Then, the pivot mechanism is attached around a joint of a patient to limit joint movement within the determined range, which can be adjusted easily during rehabilitation.

20 Claims, 8 Drawing Sheets

PIVOT MECHANISM FOR A JOINT SUPPORT

BACKGROUND OF THE INVENTION

1. Field of the Invention

The present invention relates to a pivot mechanism, and more particularly to a pivot mechanism for a joint support.

2. Description of the Prior Arts

Joints are formed between at least two adjacent bones at the knee, elbow, shoulder and the like. However, joint damage due to accident, injury, arthritis or the like may require rehabilitation. During rehabilitation, the joint damage is supported by a joint support to limit adduction, abduction, extension, flexion, intra- and extra-rotation. The joint support has a pivot mechanism. The conventional pivot mechanism has a connector and two arms. The arms mounted pivotally in the connector and each arm has teeth. The teeth engage each other so the arms synchronously rotate in a limited range.

The conventional pivot mechanism is locked by pins so medical workers must remove and adjust the pins to allow suitable range for patients. However, the adjusting the range is complicated and inconvenient so cannot be performed by patients.

To overcome the shortcomings, the present invention provides a pivot mechanism for a joint support to mitigate or obviate the aforementioned problems.

SUMMARY OF THE INVENTION

The main object of the present invention is to provide a pivot mechanism for a joint support.

A pivot mechanism for a joint support comprises a connector, a first support and a second support. The connector has multiple slots. The first support and the second support are mounted pivotally in the connector and rotate synchronously, and each has a protrusion. The protrusions are adjusted to mount in the slots of the connector and to limit an angle between the first and second support to a determined range. The pivot mechanism is attached around a joint of a patient to limit joint movement within the determined range, which can be adjusted easily during rehabilitation.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
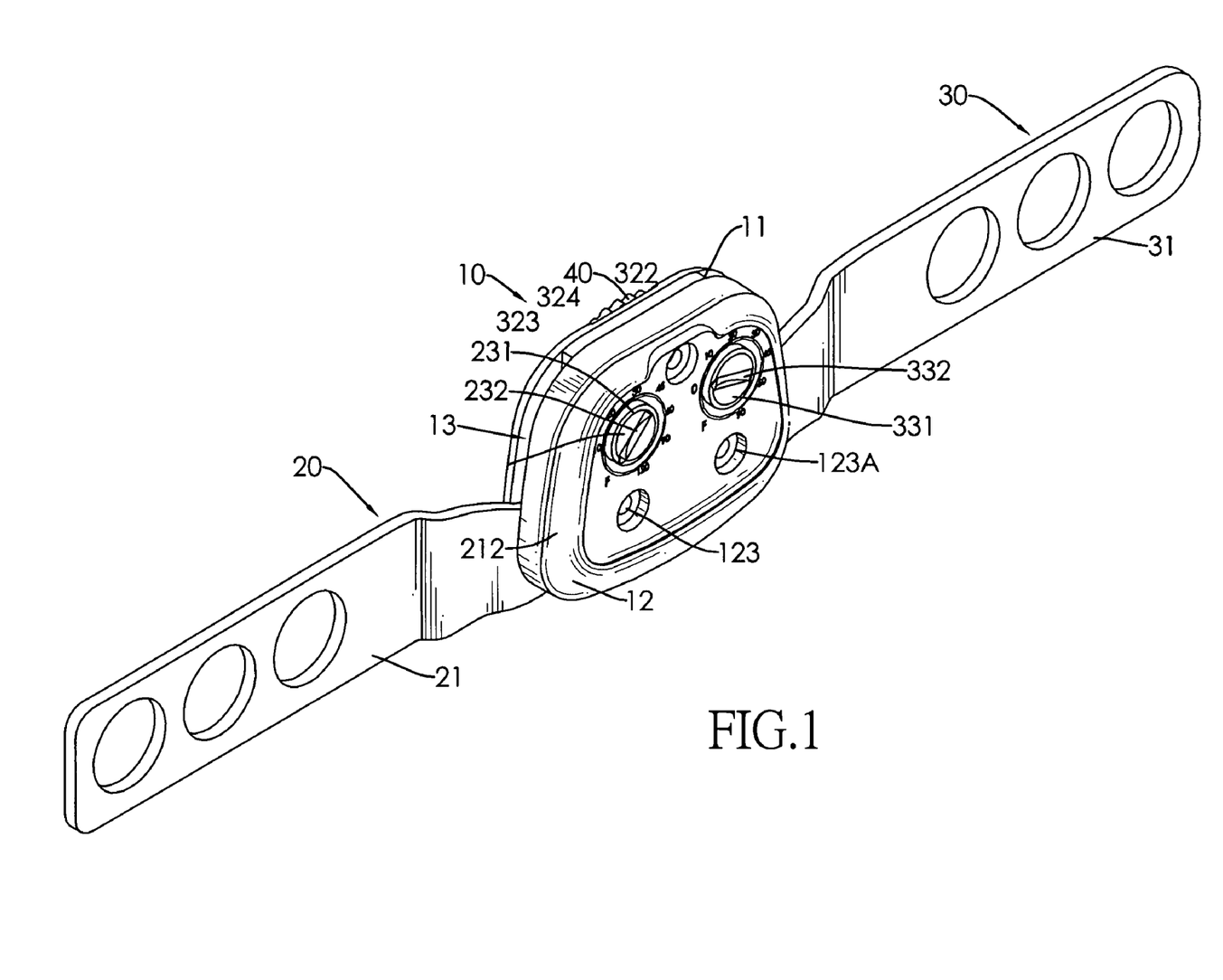
FIG. 1 is a perspective view of a pivot mechanism for a joint support in accordance with the present invention.
Figure 2:
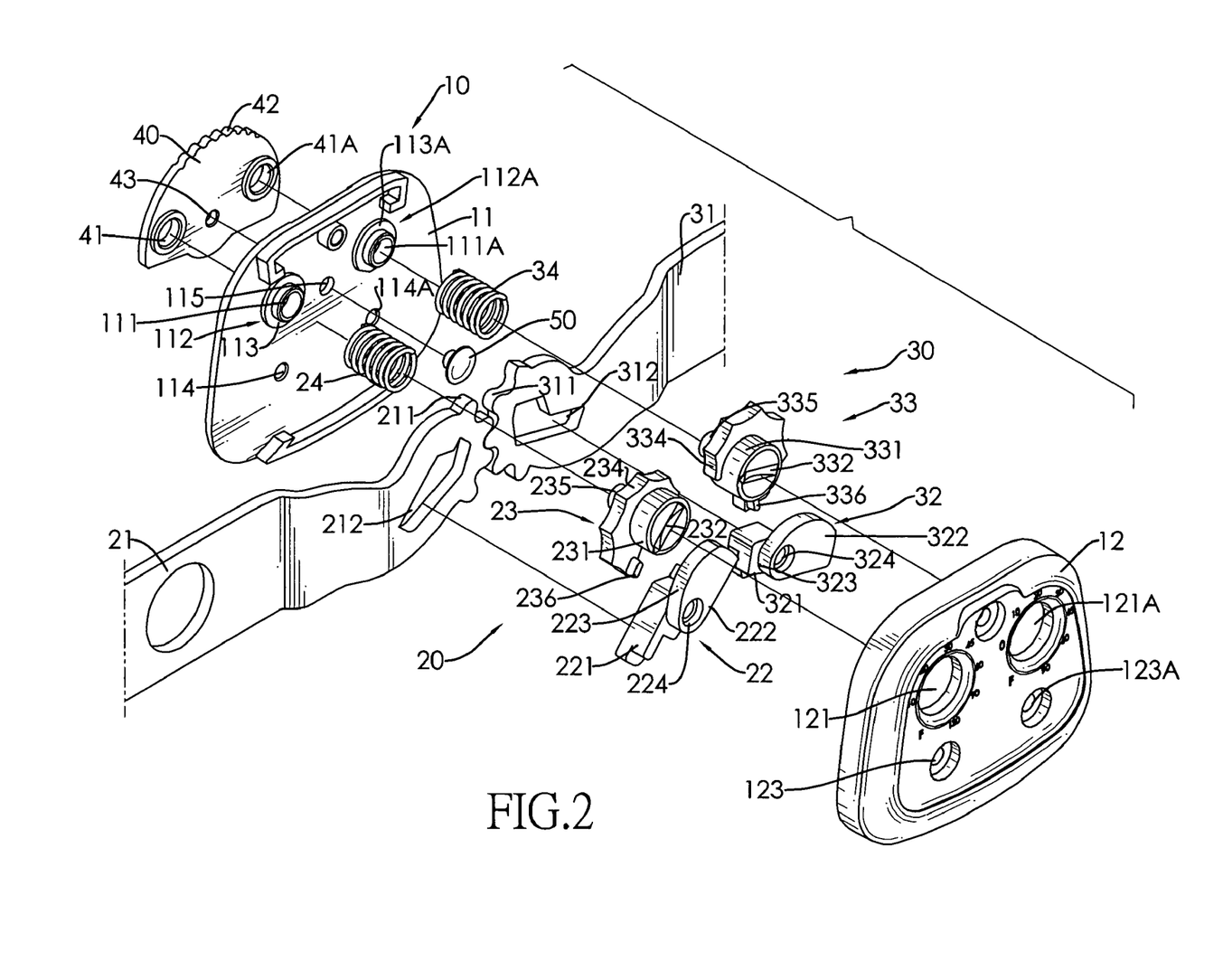
FIG. 2 is an enlarged, exploded, front perspective view of the pivot mechanism for a joint support in FIG. 1.
Figure 3:
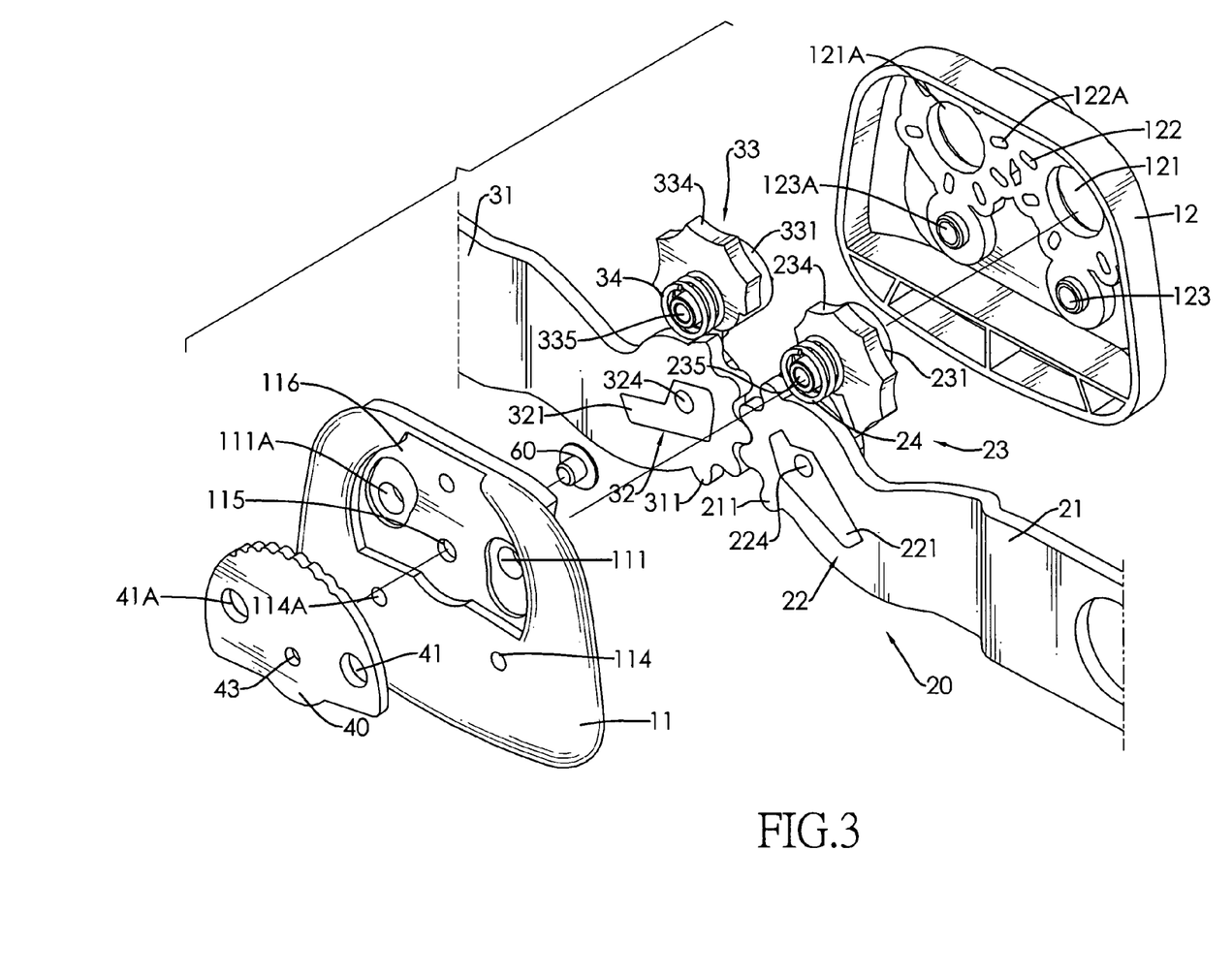
FIG. 3 is an enlarged, exploded, rear perspective view of the pivot mechanism for a joint support in FIG. 1.

With reference to FIGS. 1 to 3, a pivot mechanism for a joint support with the present invention comprises a connector (10), a first support (20), a second support (30) and a locking segment (40).

The connector (10) has a base (11), a cover (12) and a chamber (13). The base (11) has an inside, an outside, two contact holes (111,111A) and two contact rims (112,112A). The contact holes (111,111A) are formed through the base (11). The contact rims (112,112A) protrude from the inside of the base (11) and respectively formed around the contact holes (111,111A) of the base (11). The cover (12) corresponds to and is attached to the base (11) and has an inside, an outside, two contact holes (121,121A) and multiple slots (122,122A). The contact holes (121,121A) are formed through the cover (12) and respectively align with the contact holes (111,111A) of the base (11). The slots (122,122A) are formed in the inside and are arranged in a circle around the contact holes (121,121A) of the cover (12). The chamber (13) is defined between the base (11) and the cover (12) of the connector (10).

In a preferred embodiment, the base (11) further has two annular flanges (113, 113A), two positioning holes (114, 114A), a pivot hole (115) and a recess (116). The annular flanges (113, 113A) are formed respectively around the contact holes (111, 111A). The positioning holes (114,114A) and the pivot hole (115) are formed through the base (11). The recess (116) is formed in the outside of the base (11) of the connector (10) and communicates with the contact holes (111,111A) and the pivot hole (115) of the base (11). The cover (12) further has two positioning holes (123,123A). The positioning holes (123,123A) respectively align with the positioning holes (114,114A) of the base (11).

The first support (20) is connected pivotally to the connector (10) and has a first arm (21), a first linkage (22), a first dial (23) and a first spring (24). The first arm (21) has an end, first teeth (211) and a first receiving hole (212). The first teeth (211) are formed on the end of the first arm (21) and are mounted in the chamber (13) of the connector (10). The first receiving hole (212) is formed through the first arm (21) and is adjacent to the first teeth (211) of the first arm (21). The first receiving hole (212) is keyed and may be rectangular, elliptical or non-circular.

The first linkage (22) is mounted on the first arm (21) and has a first inserting part (221), a first abutting part (222) and a through hole (224). The first inserting part (221) is mounted securely in the first receiving hole (212) of the first arm (21) so the first linkage (22) and the first arm (21) move together. The first abutting part (222) is attached to the first inserting part (221) and has a curved edge (223). The through hole (224) is formed through the first inserting part (221) and the first abutting part (222) of the first linkage (22) and aligns with a corresponding positioning hole (123) of the cover (12).

The first dial (23) is mounted rotatably in the connector (10) and has an inside, an outside, a wavy edge (234), a first knob (231), a first positioning part (235) and a first positioning protrusion (236). The wavy edge (234) engages the curved edge (223) of the first abutting part (222) of the first linkage (22). The first knob (231) is attached eccentrically to the outside of the first dial (23) and protrudes from the contact hole (121) of the cover (12) of the connector (10) and has a first slot (232). The first slot (232) is formed in the first knob (231). The first positioning part (235) is a column, is attached axially to the inside of the first dial (23) and is mounted in the contact hole (111) of the base (11) of the connector (10). The first positioning protrusion (236) protrudes from the outside of the first dial (23), is adjacent to the first knob (231) and is mounted in one of the slots (122) of the cover (12) of the connector (10).

The first spring (24) is mounted around the contact rim (112) of the base (11) of the connector (10) and the positioning part (235) of the first dial (23) and has two ends. One end abuts the flange (113) of the base (11) of the connector (10). The other end abuts the first dial (23).

The second support (30) is connected pivotally to the connector (10) and has a second arm (31), a second linkage (32), a second dial (33) and a second spring (34). The second arm (31) has an end, second teeth (311) and a second receiving hole (312). The second teeth (311) are formed on the end of the second arm (31) and are mounted in the chamber (13) of the connector (10) and engage the first teeth (211) of the first arm (21). The second receiving hole (312) is formed through the second arm (31) and is adjacent to the second teeth (311) of the second support (30). The second receiving hole (312) is keyed and may be rectangular, elliptical or non-circular.

The second linkage (32) is mounted on the second arm (31) and has a second inserting part (321), a second abutting part (322) and a through hole (324). The second inserting part (321) is mounted securely in the second receiving hole (312) of the second arm (31) so the second linkage (32) and the second arm (31) move together. The second abutting part (322) is attached to the second inserting part (321) and has a curved edge (323). The through hole (324) is formed through the second inserting part (321) and the second abutting part (322) of the second linkage (32) and aligns with a corresponding positioning hole (123A) of the cover (12).

The second dial (33) is mounted rotatably in the connector (10) and has an inside, an outside, a wavy edge (334), a second knob (331), a second positioning part (335) and a second positioning protrusion (336). The wavy edge (334) engages the curved edge (323) of the second abutting part (322) of the second linkage (32). The second knob (331) is attached eccentrically to the outside of the second dial (33) and protrudes from the contact hole (121A) of the cover (12) of the connector (10) and has a second slot (332). The second slot (332) is formed in the second knob (331). The second positioning part (335) is a column, is attached axially to the inside of the second dial (33) and is mounted in the contact hole (111A) of the base (11) of the connector (10). The second positioning protrusion (336) protrudes from the outside of the first dial (23), is adjacent to the second knob (331) and is mounted in one of the slots (122A) of the cover (12) of the connector (10).

The second spring (34) is mounted around the contact rim (112A) of the base (11) of the connector (10) and the positioning part (335) of the second dial (33) and has two ends. One end abuts the flange (113A) of the base (11) of the connector (10). The other end abuts the second dial (33).

The locking segment (40) is mounted pivotally in the recess (116) of the base (11) of the connector (10) and has an edge and two holes (41,41A). The holes (41,41A) are formed through the locking segment (40) and respectively align with the contact holes (111,111A). In a preferred embodiment, the locking segment (40) has teeth (42) and a pivot hole (43). The teeth (42) are formed on the edge of the locking segment (40). The pivot hole (43) is formed through the locking segment (40) and between the holes (41,41A) and aligns with the pivot hole (115) of the base (11) of the connector (10).

A fastener is mounted through the positioning hole (123) of the cover (12) and the through hole (224) of the first linkage (22) and is further mounted in the positioning hole (114) of the base (11). Another fastener is mounted through the positioning hole (123A) of the cover (12) and the through hole (324) of the second linkage (32) and is further mounted in the positioning hole (114A) of the base (11).

Figure 4:
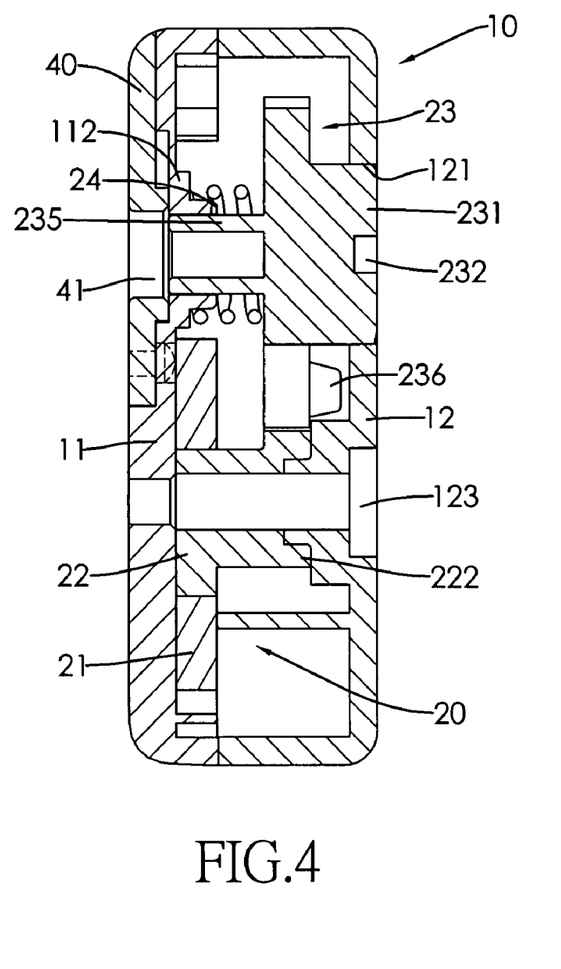
FIG. 4 is a side view in partial section of the pivot mechanism for a joint support in FIG. 1.

With reference to FIGS. 2 and 4, the first arm (21) and the second arm (31) are adjusted to, an adjustment angle from a normal line of the connector (10). The first linkage (21) disengages the first dial (23) and the second linkage (31) disengages the second dial (33). The first arm (21) and the second arm (31) rotate relatively until the first linkage (21) engages the first dial (23) or the second linkage (31) engages the second dial (33). The first arm (21) and the second arm (31) are limited by an adjusted angle.

Figure 5:
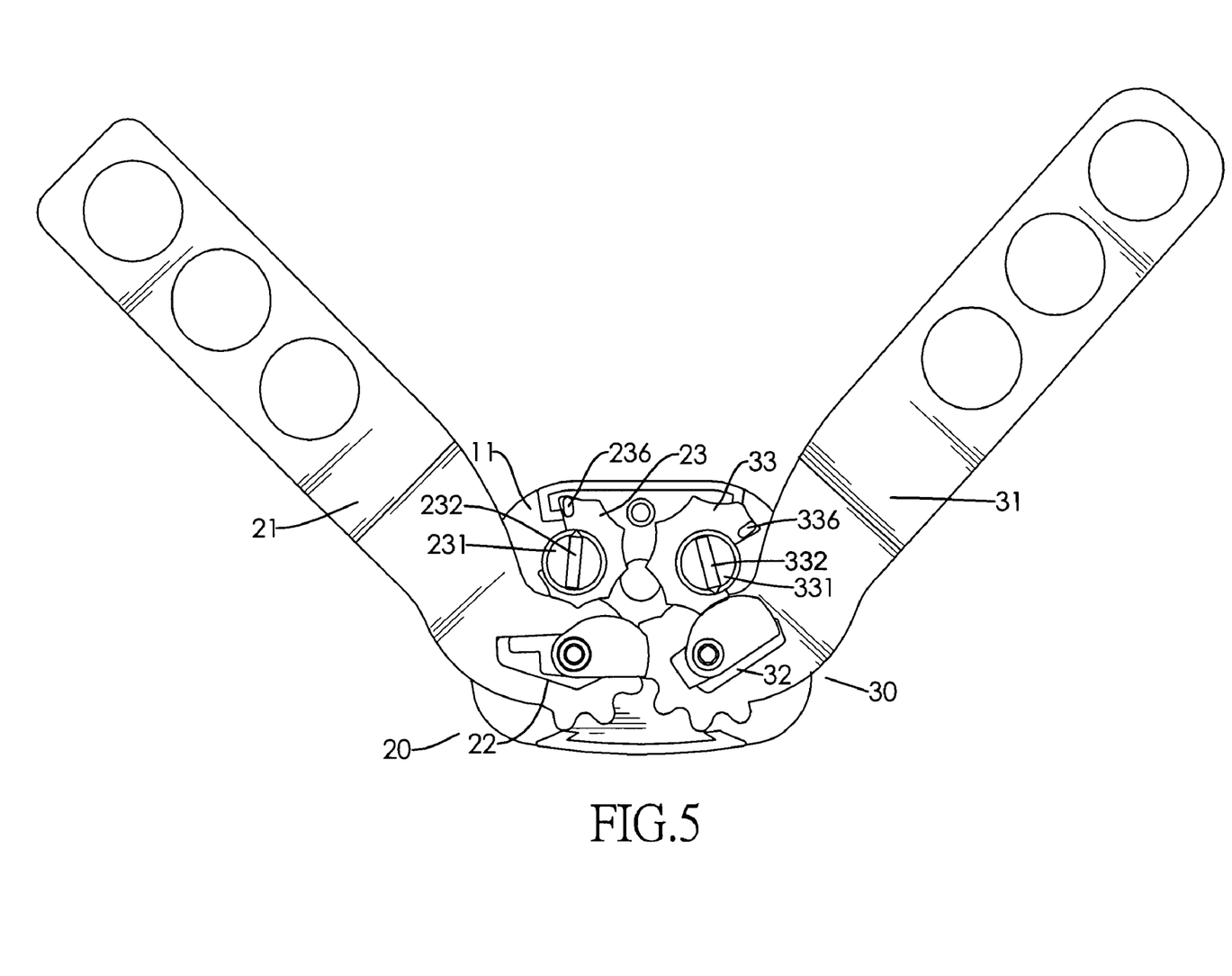
FIG. 5 is an operational front view of internal elements of the pivot mechanism for a joint support in FIG. 1.

With reference to FIGS. 2, 3 and 5, a tool such as a coin, key, screwdriver or the like may be used to engage the first slot (232) of the first dial (23) and presses the first dial (23). The first positioning protrusion (236) of the first dial (23) disengages from the slot (122) of the cover (12) and the first spring (24) is compressed to have spring force. The first dial (23) is rotated to adjust by a suitable degree. The tool is removed from the first slot (232) of the first dial (23) and releases the first dial (23). The first spring (24) provides resilient force to the first dial (23). The first positioning protrusion (236) of the first dial (23) engages another corresponding slot (122) of the cover (12). Because of the first knob (231) is attached eccentrically to the first dial (23), the first knob (231) of the first dial (23) is rotated by a different degree to limit the first arm (21) rotating angle. Similarly, the second arm (31) may also be adjusted.

Figure 6:
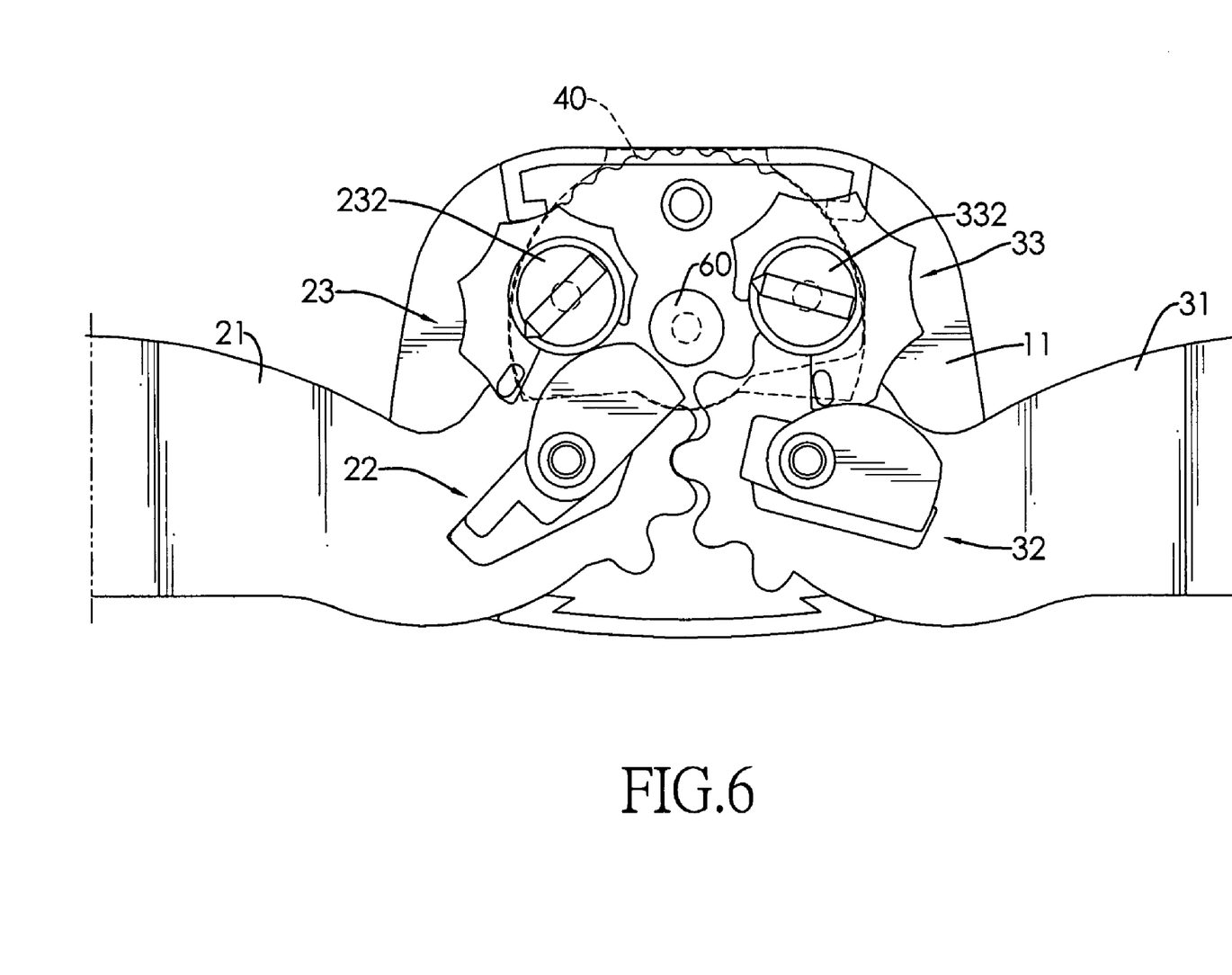
FIG. 6 is a partially operational enlarged front view of internal elements of the pivot mechanism for a joint support in FIG. 1.
Figure 7:
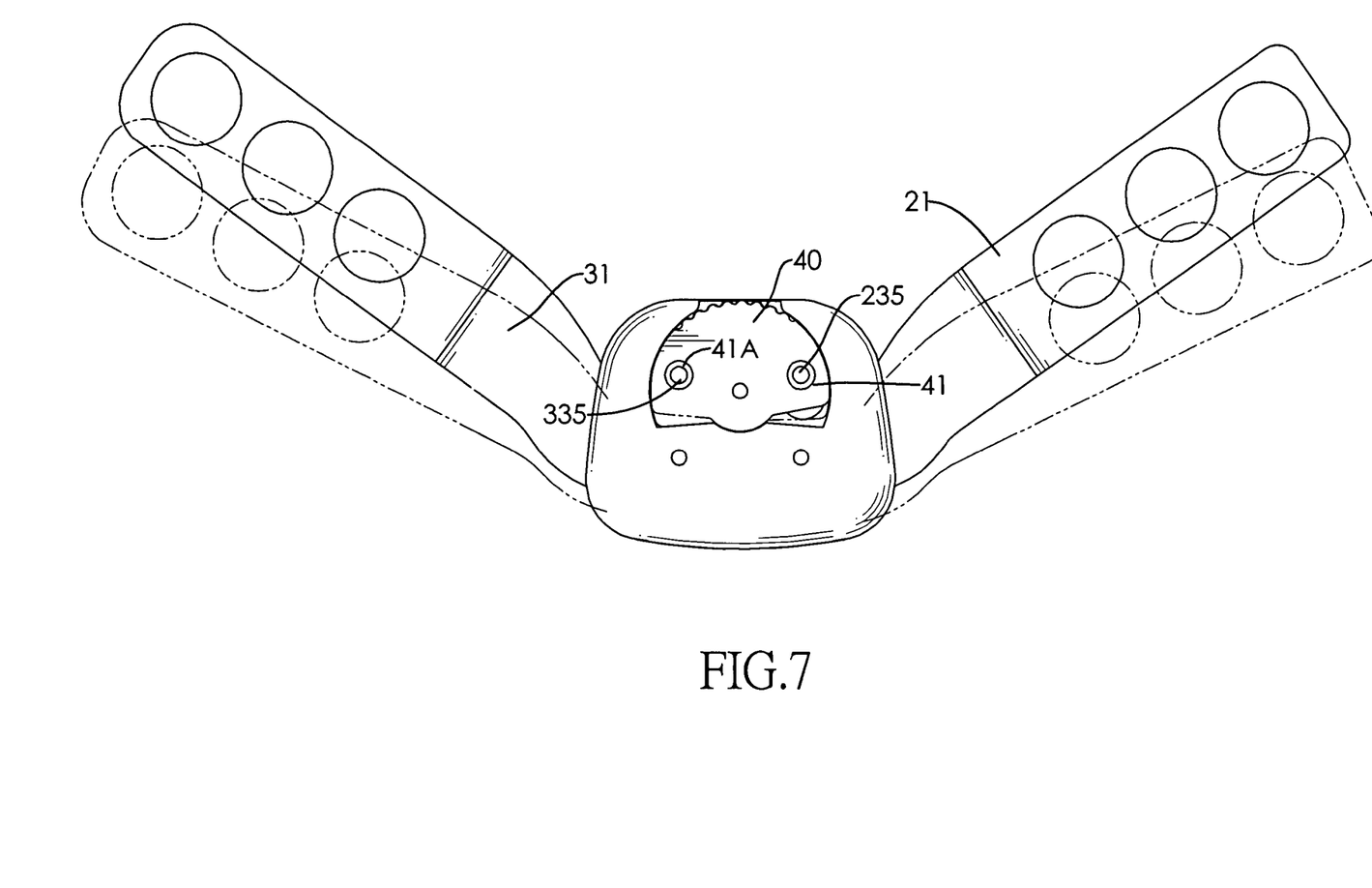
FIG. 7 is an operational rear view of the pivot mechanism for a joint support in FIG. 1, showing movement of the first and second support.

With reference to FIGS. 4, 6 and 7, when the first knob (231) of the first dial (23) is pressed, the first positioning part (235) of the first dial (23) is pressed and protrudes from the contact hole (111) of the base (11) and is in the hole (41) of the locking segment (40). When the first knob (231) of the first dial (23) is released the first spring (24) provides a resilient force to push the first positioning part (235) of the first dial (23) away from entering into the hole (41) of the locking segment (40). After the locking segment (40) being pivoted, and the hole (41) of the locking segment (40) misaligns with the contact hole (111) of the base (11). Consequently, the first dial (23) is kept from being pressed because the first positioning part (235) of the first dial (23) is blocked by the locking segment (40). Accordingly, the first positioning protrusion (236) of the first dial (23) is kept engaging and not disengaging from the slot (122) of the cover (12) so the first knob (231) of the dial (23) can not be rotated. The locking segment (40) effectively avoids the angle between the first arm (21) and the second arm (32) to be changed accidentally. Besides, the teeth (42) of the locking segment (40) offer friction for operating conveniently.

Figure 8:
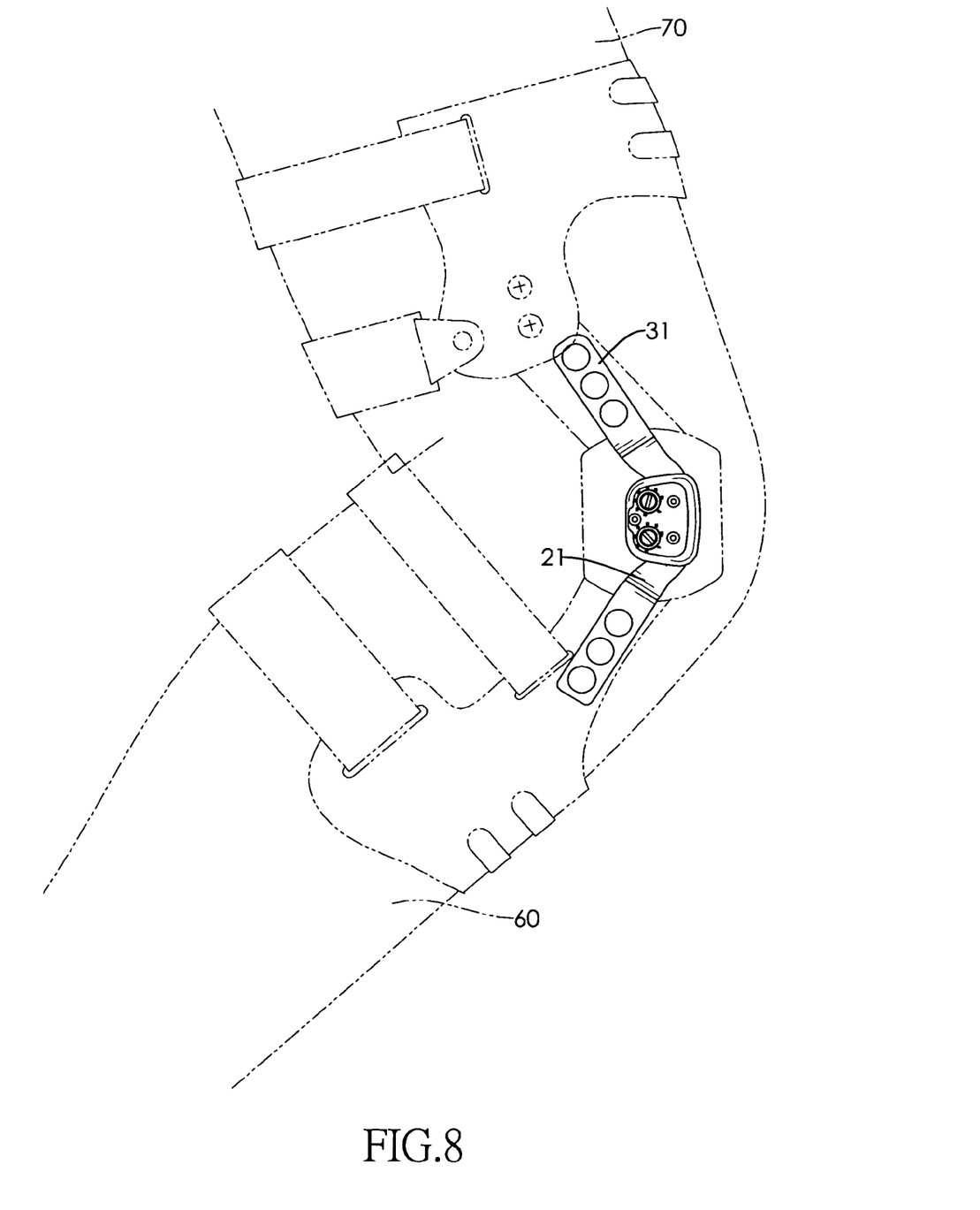
FIG. 8 is an operational front view of the pivot mechanism for a joint support in FIG. 1 shown mounted to a knee support attached to a knee joint.

Medical workers can change the adjustment angles of the first arm (21) and the second arm (31) for different patients or different cases. With reference to FIG. 8, the first arm (21) and the second arm (31) are respectively positioned on a shank (60) and a thigh (70). The shank (60) and the thigh (70) move with the first arm (21) and the second arm (31). The range of activity of the shank (60) and the thigh (70) are limited in a safety range. Therefore, the pivot mechanism for a joint support in accordance with the present invention is adapted for patients. Moreover, the process to adjust the angle is easy and convenient by rotating the first dial (23) and the second dial (33).

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A pivot mechanism for a joint support comprising:
    a connector having
        a chamber; and
        multiple slots formed in the connector;
    a first support connected pivotally to the connector and having
        a first arm having
            an end; and
            first teeth formed on the end of the first arm and mounted in the chamber of the connector;
        a first linkage mounted in the first arm;
        a first dial mounted rotatably in the connector and having
            an inside;
            an outside;
            a first knob attached to the outside of the first dial; and
            a first positioning protrusion protruding from the outside of the first dial, adjacent to the first knob and mounted in one of the slots of the connector;
        a first spring mounted around the first dial; and
    a second support connected pivotally to the connector and having
        a second arm having
            an end;
            second teeth formed on the end of the second arm and mounted in the chamber of the connector and engaging the first teeth of the first arm;
        a second linkage mounted in the second arm;
        a second dial mounted rotatably in the connector and having
            an inside;
            an outside;
            a second knob attached to the outside of the second dial; and
            a second positioning protrusion protruding from the outside of the first dial, adjacent to the second knob and mounted in one of the slots of the connector; and
        a second spring mounted around the second dial.

2. The pivot mechanism for a joint support as claimed in claim 1, wherein
    the first dial of the first support further has a first positioning part attached to the inside of the first dial and mounted through the first spring; and
    the second dial of the second support further has a second positioning part attached to the inside of the second dial and mounted through the second spring.

3. The pivot mechanism for a joint support as claimed in claim 2, wherein
    the first knob is attached to the first dial eccentrically; and
    the second knob is attached to the second dial eccentrically.

4. The pivot mechanism for a joint support as claimed in claim 2 further has a locking segment mounted pivotally on the connector.

5. The pivot mechanism for a joint support as claimed in claim 2, wherein
    the first arm of the first support further has a first receiving hole formed through the first arm adjacent to the first teeth of the first arm;
    the first linkage of the first support further has
        a first inserting part mounted securely in the first receiving hole of the first arm; and
        a first abutting part attached to the first inserting part and engaging the first dial; and
    the second arm of the second support further has a second receiving hole formed through the second arm adjacent to the second teeth of the second arm;
    the second linkage of the second support further has
        a second inserting part mounted securely in the second receiving hole of the first arm; and
        a second abutting part attached to the second inserting part and engaging the second dial.

6. The pivot mechanism for a joint support as claimed in claim 5, wherein
    the first knob is attached to the first dial eccentrically; and
    the second knob is attached to the second dial eccentrically.

7. The pivot mechanism for a joint support as claimed in claim 5 further has a locking segment mounted pivotally on the connector.

8. The pivot mechanism for a joint support as claimed in claim 5, wherein
    the first abutting part of the first linkage has a curved edge;
    the first dial further has a wavy edge engaging the curved edge of the first abutting part of the first arm;
    the second abutting part of the second linkage has a curved edge; and
    the second dial further has a wavy edge engaging the curved edge of the second abutting part of the second arm.

9. The pivot mechanism for a joint support as claimed in claim 8 further has a locking segment mounted pivotally on the connector.

10. The pivot mechanism for a joint support as claimed in claim 8, wherein
    the first knob is attached to the first dial eccentrically; and
    the second knob is attached to the second dial eccentrically.

11. The pivot mechanism for a joint support as claimed in claim 1, wherein
    the first arm of the first support further has a first receiving hole formed through the first arm adjacent to the first teeth of the first arm;
    the first linkage of the first support further has
        a first inserting part mounted securely in the first receiving hole of the first arm; and
        a first abutting part attached to the first inserting part and engaging the first dial; and
    the second arm of the second support further has a second receiving hole formed through the second arm adjacent to the second teeth of the second arm;
    the second linkage of the second support further has
        a second inserting part mounted securely in the second receiving hole of the first arm; and
        a second abutting part attached to the second inserting part and engaging the second dial.

12. The pivot mechanism for a joint support as claimed in claim 11, wherein
    the first knob is attached to the first dial eccentrically; and
    the second knob is attached to the second dial eccentrically.

13. The pivot mechanism for a joint support as claimed in claim 11 further has a locking segment mounted pivotally on the connector.

14. The pivot mechanism for a joint support as claimed in claim 11, wherein
    the first abutting part of the first linkage has a curved edge;
    the first dial further has a wavy edge engaging the curved edge of the first abutting part of the first arm;
    the second abutting part of the second linkage has a curved edge; and
    the second dial further has a wavy edge engaging the curved edge of the second abutting part of the second arm.

15. The pivot mechanism for a joint support as claimed in claim 14 further has a locking segment mounted pivotally on the connector.

16. The pivot mechanism for a joint support as claimed in claim 14, wherein
    the first knob is attached to the first dial eccentrically; and
    the second knob is attached to the second dial eccentrically.

17. The pivot mechanism for a joint support as claimed in claim 1, wherein
    the first knob is attached to the first dial eccentrically; and
    the second knob is attached to the second dial eccentrically.

18. The pivot mechanism for a joint support as claimed in claim 17 further has a locking segment mounted pivotally on the connector.

19. The pivot mechanism for a joint support as claimed in claim 1 further has a locking segment mounted pivotally on the connector.

20. The pivot mechanism for a joint support as claimed in claim 19, wherein
    the connector further has a recess formed in the connector; and
    the locking segment is mounted and rotates in the recess of the connector.

* * * * *